(12) United States Patent
Khanna (10) Patent No.: US 8,915,946 B2
(45) Date of Patent: Dec. 23, 2014

(54) LAMINOPLASTY SYSTEM

(76) Inventor: Rohit Khanna, Daytona Beach, FL (US)

( * ) Notice: Subject to any disclaimer, the term of this patent is extended or adjusted under 35 U.S.C. 154(b) by 691 days.

(21) Appl. No.: 12/917,481

(22) Filed: Nov. 2, 2010

(65) Prior Publication Data

US 2011/0046680 A1 Feb. 24, 2011

Related U.S. Application Data (63) Continuation of application No. 10/299,624, filed on Nov. 19, 2002, now Pat. No. 6,660,007, which is a continuation of application No. 10/035,281, filed on Jan. 3, 2002, now abandoned.

(51) Int. Cl.
*A61B 17/88* (2006.01)
*A61B 17/70* (2006.01)

(52) U.S. Cl.
CPC .................................. *A61B 17/7071* (2013.01)
USPC ....................................................... 606/279

(58) Field of Classification Search
USPC .......................... 606/246, 248, 249, 279, 86 R
See application file for complete search history.

(56) References Cited

U.S. PATENT DOCUMENTS

| | | | |
|---|---|---|---|
| 5,405,391 A * | 4/1995 | Hednerson et al. | ........ 623/17.15 |
| 5,620,448 A | 4/1997 | Puddu | |
| 5,888,223 A | 3/1999 | Bray, Jr. | |
| 5,980,572 A | 11/1999 | Kim et al. | |
| 6,066,175 A | 5/2000 | Henderson et al. | |
| 6,080,157 A | 6/2000 | Cathro et al. | |
| 6,235,059 B1 | 5/2001 | Benezech et al. | |
| 6,241,771 B1 | 6/2001 | Gresser et al. | |
| 6,544,266 B1 | 4/2003 | Roger et al. | |
| 6,635,087 B2 | 10/2003 | Angelucci et al. | |
| 6,660,007 B2 | 12/2003 | Khanna | |
| 6,712,852 B1 | 3/2004 | Chung et al. | |
| 6,997,953 B2 | 2/2006 | Chung et al. | |
| 7,264,620 B2 | 9/2007 | Taylor | |
| 2003/0125738 A1 | 7/2003 | Khanna | |
| 2004/0030388 A1 | 2/2004 | Null | |
| 2005/0131412 A1 | 6/2005 | Olevsky | |

* cited by examiner

*Primary Examiner* — Anu Ramana (57) ABSTRACT

Fixation devices and methods for stabilization of the lamina after laminoplasty are described. The device comprises of a plate with several holes that receive bone fasteners. The plate is curved at the ends to contour to the vertebral structure and has appendages to engage the displaced lamina in a fixed position. Alternatively, the plate has a bone fusion spacer in the middle to engage and fuse the lamina in the displaced position. Several methods of dynamically stabilizing the lamina after either the open door, double door or expansive laminoplasty technique are provided.

18 Claims, 12 Drawing Sheets

LAMINOPLASTY SYSTEM

RELATED U.S. APPLICATION DATA

This application is a continuation of U.S. application Ser. No. 10/299,624, which was filed on Nov. 19, 2002, and issued as U.S. Pat. No. 6,660,007 on Dec. 9, 2003, which was filed as a continuation of U.S. application Ser. No. 10/035,281 and filed on Jan. 3, 2002, now abandoned, and herein incorporated by reference.

BACKGROUND OF THE INVENTION

Cervical stenosis with spinal cord compression and consequent myelopathy is a very common problem encountered by the spine surgeon. The usual cause of multilevel cervical stenosis is spondylosis and/or ossification of the posterior longitudinal ligament. Surgical decompression either through an anterior or posterior approach can be undertaken.

An anterior approach usually involves multilevel corpectomy with fusion and stabilization. The main drawback of this technique is the increased time and complexity of the procedure as well as the risk of pseudoarthrosis and accelerated degeneration at the levels above and below the fusion.

A posterior approach has traditionally involved a simple laminectomy, laminectomy with facet fusion, or laminoplasty. The drawback of a simple laminectomy is the risk of late clinical deterioration form either kyphosis or postlaminectomy scar formation. Laminectomy with facet fusion decreases the risk of kyphosis but it also decreases the range of motion in the spine and increases the risk of accelerated degeneration at the levels above and below the fusion.

Laminoplasty either through open door or double door technique provides greater stability and range of motion when compared with laminectomy alone. This technique entails laminoplasty for decompression and fixation with a plate with or without laminar fusion. The principle behind laminar fixation is that it maintains the decompression following laminoplasty as well as the displaced lamina in a fixed position thereby providing stabilization also.

U.S. patent application Ser. No. 10/035,281 describes several laminar fixation plates with and without a bone fusion spacer that allow for lamina fixation and/or fusion. U.S. Pat. No. 6,660,007 describes laminoplasty plates for open door and double door techniques with a spacer in the middle to maintain the decompressed lamina position.

The present invention is an apparatus for use in either the open door or double door laminoplasty technique to stabilize the lamina in the spine thereby preserving the range of motion as well as maintaining stability.

SUMMARY OF THE INVENTION

The present invention relates a laminar fusion and fixation system following either open door or double door laminoplasty technique. This system with the spacer and plate reduces surgical time and simplifies laminar fixation and fusion if needed after laminoplasty.

In one embodiment the lamina fixation device consists of a plate angled at each end with a bone engaging appendage. The plate length can be variable with uniform width and thickness specific for the cervical, thoracic or lumbar spine. The angled ends of the plate allows screw placement in the lamina or spinous process on one side and the facet on the other side. The appendage shape can be straight, curved, or contoured with a notch to encase the lamina edge and allow securement to the lamina on one side and the lateral mass or facet on the other side. This implant is made of titanium or similar alloy with magnetic resonance imaging compatibility.

Alternatively, the implant is made of allograft bone, hydroxyapatite, or similar absorbable fusion material. The implant can also be made of a radiolucent material like polyaryletherketone or polyetheretherketone (PEEK).

In another embodiment the invention relates a laminar fusion and fixation system following laminoplasty. The invention comprises a plate made of titanium or similar alloy with magnetic resonance imaging compatibility which is contoured at the edges to allow fixation of the lamina and securement of the bone fusion spacer. The contoured design of the plate allows screw placement in the lamina and/or facets. The spacer longitudinal ends can be contoured with a notch to allow securement to the lamina on one side and the lateral mass or facet on the other side. The contoured end shape can be curved, straight, or any other shape to encase and secure the lamina or facet edge. The spacer can be made of allorgraft bone, autograft bone, xenograft bone, or a resorbable fusion material like hydroxyapatite which is eventually resorbed and replaced with autologous bone during the fusion process.

In another embodiment the allograft bone or resorbable graft and plate are constructed as a unit with the bone graft attached to the plate in the middle through either screws or an adhesive material.

In another embodiment, the bone graft and plate are designed for laminar fusion and fixation following double door laminoplasty. The bone graft in the middle allows for laminar fusion in the decompressed position with the plate design bent on both ends securing the graft to the lamina.

The procedure as would be undertaken with the use of the laminoplasty fixation system is described as follows. An open door laminoplasty entails creating a gutter at the junction of the lamina and medial aspect of the facet on both sides with the use of a drill. On the side of the laminoplasty opening, the drilling is carried through into the canal or the opening completed with a small kerrison rongeur. At the other side, the inner cortex at the lamina and facet junction is not drilled. The lamina at the open end is elevated and the spinous process pushed away in order to create a greenstick osteotomy and allow for the laminoplasty decompression. Typically, between 6-20 mm of distraction between the lamina and the facet provides for a good spinal decompression. In order to maintain the position of the lamina, the pre-contoured laminar fixation plate with the attached bone fusion spacer is positioned between the lamina and the facet. The spacer maintains the displaced position of the lamina and the plates with the contoured ends secure the construct via screws to the lamina and facet. In another embodiment of the laminoplasty fixation device, the plate has appendages instead of a spacer perpendicular to the longitudinal plate axis which engage the lamina and the facet and increase the extent of the spinal canal space.

A trap door or double door laminoplasty is created by drilling on each side at the laminar and lateral mass junction the outer laminar cortex and sparing the inner laminar cortex. The spinous process is resected or split and a midline gutter is also created which extends through the inner cortex which can be opened with a small kerrison rongeur. The lamina on either side are lifted and opened creating a greenstick osteotomy on each side. In order to maintain the decompressed position of the lamina, a contoured plate attached to a bone fusion spacer is placed in between the split lamina. The plate can either be fixated with screws to the lamina or the facets. In another embodiment, the plate has appendages instead of a spacer perpendicular to the longitudinal plate axis which engage the lamina and increase the extent of the spinal canal space.

A minimally invasive approach is undertaken with small incisions and serial dilation of the soft tissue along with splitting of the paraspinal muscles from the skin to the spine. A tubular port or any other shape retractor is then placed to maintain the exposure. The drilling of the lamina and, if needed, the spinous process is undertaken with this exposure using either an endoscope or a microscope magnification and subsequently the lamina are displaced to widen the spinal canal. A laminoplasty implant is then placed and secured to the lamina and facet. The tubular port is then removed and the skin incision closed. Intra-operative x-rays or a navigation system can be used to localize the spine level and confirm correct implant placement.

Another variation on the open door laminoplasty is the expansive laminoplasty most suited for the thoracolumbar spine. In this method, the lamina on either side at the junction of the facets are drilled and opened. A lateral spinal canal recess decompression and/or foraminotomy is undertaken and the lamina replaced with the spacer construct on both sides.

Embodiments of the laminoplasty implants also describe a spacer portion and one or more bendable lamina engagement portions in order to conform to the anatomy of a particular patient. The spacer portions and/or lamina engagement portions can also be pre-bent to accommodate patient anatomy based on anatomical considerations encountered during surgery. The spacer has open ends along the longitudinal plate axis and in other embodiments can also contain open top end to pack the spacer with bone fusion material after implantation and set expansion of the spacer. The bottom end of the spacer is solid and prevents any bone fusion material to migrate into the spinal canal.

Various embodiments and advantages of the current invention are set forth in the following detailed description and claims which will be readily apparent to one skilled in the art.

DETAILED DESCRIPTION OF THE EMBODIMENTS

Figure 1:
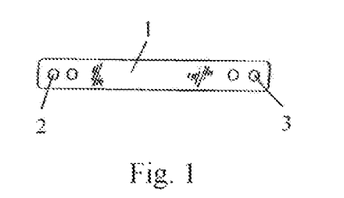
FIG. 1 is a top view of one embodiment of the plate.
Figure 2:
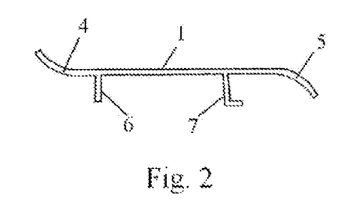
FIG. 2 is a side view of the plate.
Figure 3:
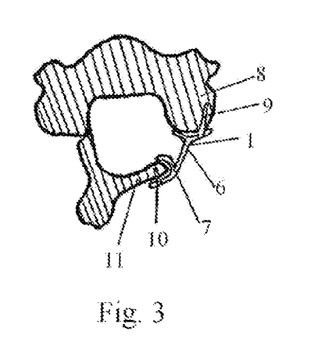
FIG. 3 is a cross section of the vertebra following an open door laminoplasty with the plate shown in FIG. 2 in place.
Figure 4:
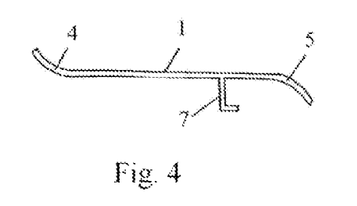
FIG. 4 is a side view of another embodiment of the plate.
Figure 5:
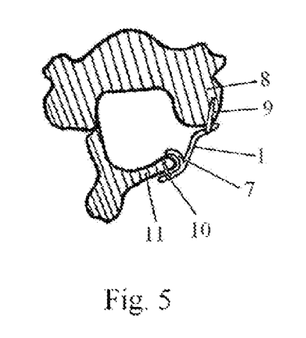
FIG. 5 is a cross section of the vertebra following an open door laminoplasty with the plate shown in FIG. 4 in place.

The technique of open-door laminoplasty stabilization without laminar fusion undertaken with the use of the plates is illustrated in FIGS. 1-5. The plate has a top surface 1 with bone screw holes at the ends 2 and 3. The ends have an upward angle at one end 4 and downward angle at the other 5. In one embodiment as seen on the side view in FIG. 2, there is a hook appendage 7 perpendicular to the plate to engage the lamina at one end and a straight appendage 6 at the other end to secure to the facet. In another embodiment of the plate as seen in FIG. 4, there is only one appendage 7 at the end prior to the downward angle of the plate. The implanted construct is seen in FIGS. 3 and 5. The plate is secured to the lamina 11 via bone screw 10 and facet 8 via bone screw 9. The hook 7 secures the lamina in the displaced laminoplasty position. As seen in FIG. 3, the additional straight appendage 6 at the facet end allows the plate to rest on the facet 8.

Figure 6:
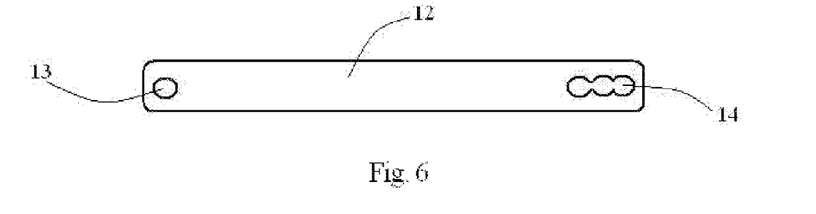
FIG. 6 is a top view of another embodiment of the plate.
Figure 7:
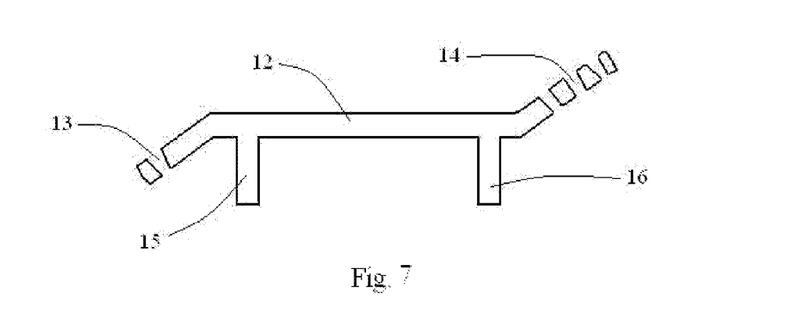
FIG. 7 is a sectional side view of the plate.
Figure 8:
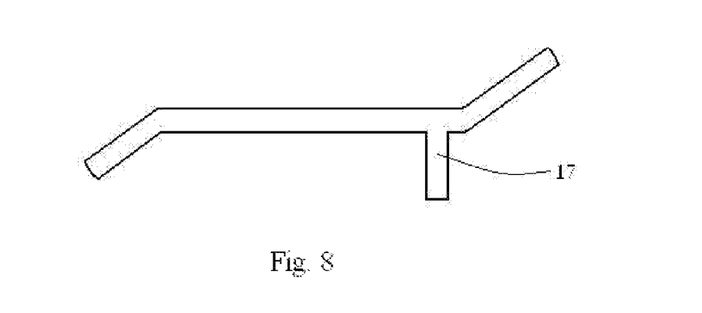
FIG. 8 is a side view of another embodiment of the plate.
Figure 9:
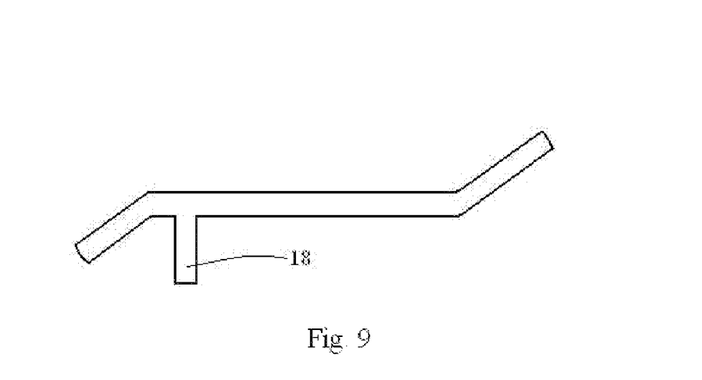
FIG. 9 is a side view of another embodiment of the plate.
Figure 10:
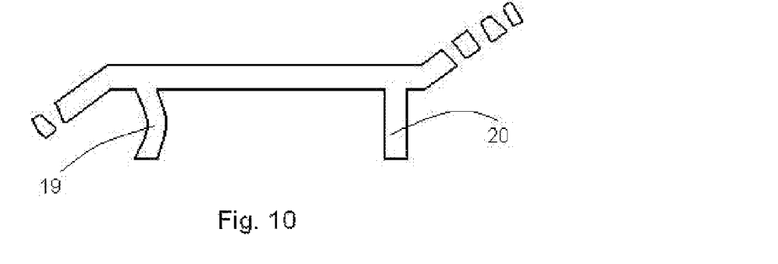
FIG. 10 is a sectional side view of another embodiment of the plate.
Figure 11:
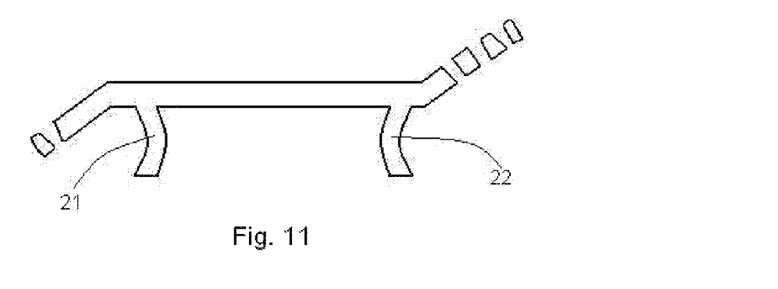
FIG. 11 is a sectional side view of another embodiment of the plate.
Figure 12:
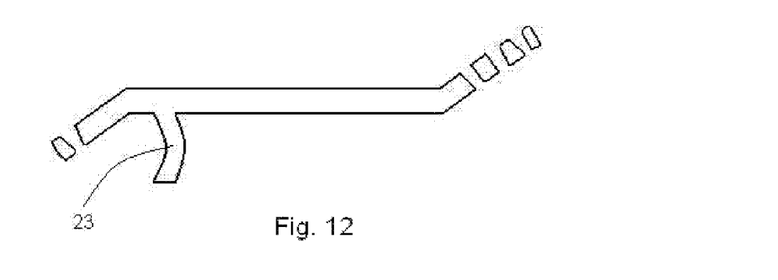
FIG. 12 is a sectional side view of another embodiment of the plate.
Figure 13:
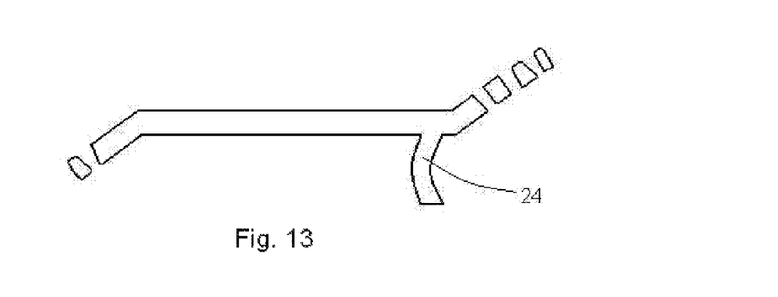
FIG. 13 is a sectional side view of another embodiment of the plate.
Figure 17:
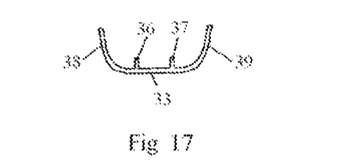
FIG. 17 is a side view of the plate.

In another embodiment, the plate 12 as shown in FIG. 6 comprises a lamina engaging portion with screw hole 13 and facet engaging portion with multiple screw holes. The plates can have straight appendages 15 and 16 prior to the angle at both sides as shown in FIG. 7, a straight appendage 17 on the facet side as shown in FIG. 17, a straight appendage 18 on the lamina side as shown in FIG. 9, a curved appendage 19 at the lamina side and a straight appendage 20 at the facet side as shown in FIG. 10, curved appendages 21 and 22 prior to the angle at both sides as shown in FIG. 11, a curved appendage only 23 at the lamina side as shown in FIG. 12, or a curved appendage 24 at the facet side as shown in FIG. 13.

Figure 14:
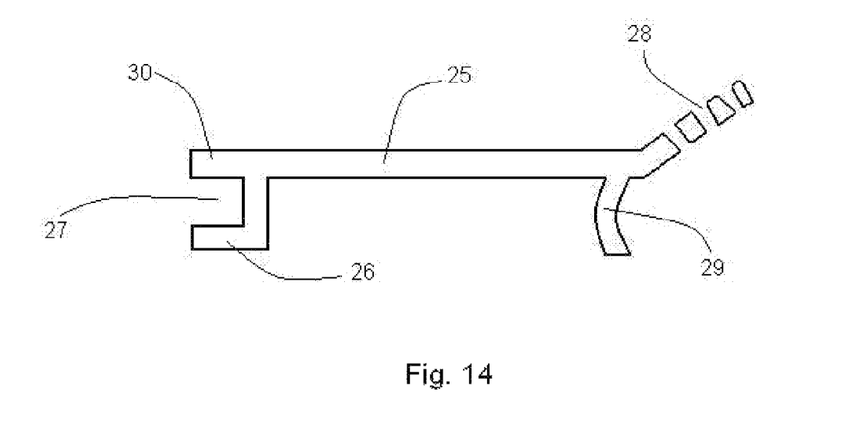
FIG. 14 is a sectional side view of another embodiment of the plate.
Figure 15:
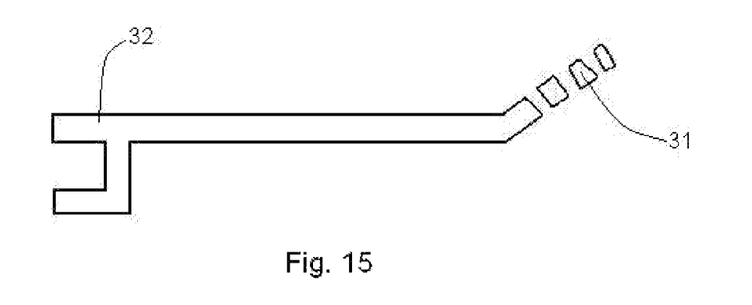
FIG. 15 is a sectional side view of another embodiment of the plate.

In another embodiment as shown in FIG. 14, the plate has a central portion 25, a lamina engaging end 30 and a facet engaging end with screw holes 28. The lamina engaging end 30 has a hook extension 26 which engages the lamina end into the space 27. The facet engaging end also has a perpendicular extension 29. In a variation of the above embodiment as seen in FIG. 15, comprising of a lamina engaging end 32 and a facet engaging end 31 without an appendage. Other embodiments of the plate can comprise of spikes or clamps at the lamina or facet bone engaging ends with or without screw placement.

Figure 16:
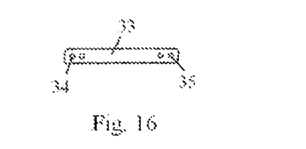
FIG. 16 is a top view of another embodiment of the plate.
Figure 20:
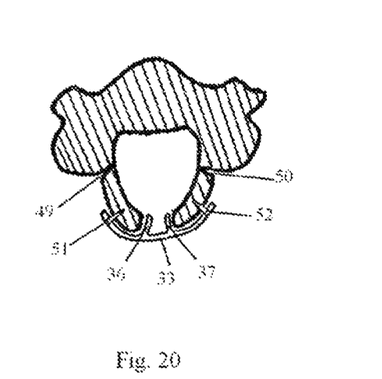
FIG. 20 is a cross section of the vertebra following a trap door laminoplasty with the plate shown in FIG. 17 in place.

For the trap-door technique of laminoplasty, stabilization without laminar fusion is undertaken with the use of the plates alone. In one embodiment of the plate as illustrated in FIGS. 16 and 17, the plate has a top surface 33 and screw holes at both ends 34 and 35. The appendages 36 and 37 secure the displaced lamina and the curvatures at both ends 38 and 39 allow attachment to the lamina. The implanted plate is shown in FIG. 20 with bone screws 51 and 52 securing it to the lamina on both sides.

Figure 18:
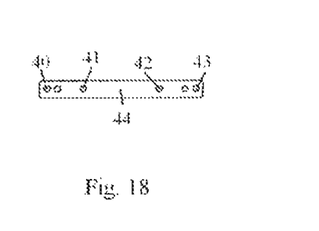
FIG. 18 is a top view of another embodiment of the plate.
Figure 19:
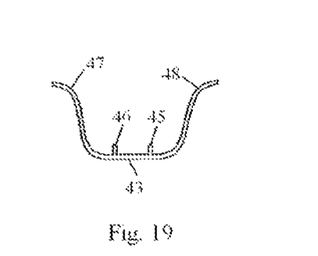
FIG. 19 is a side view of the plate.
Figure 21:
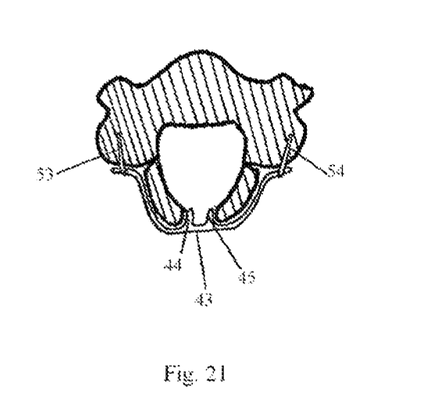
FIG. 21 is a cross section of the vertebra following a trap door laminoplasty with the plate shown in FIG. 19 in place.

In another embodiment as illustrated in FIGS. 18 and 19, the plate is curved at the ends 47 and 48. The plate has a top surface 44 with bone screw holes 41 and 42 for laminar fixation and holes 40 and 43 for facet fixation on both sides. The appendages 45 and 46 secure the displaced lamina. The implanted plate is shown in FIG. 21 with bone screws 53 and 54 securing it to the facets on both sides.

Figure 22:
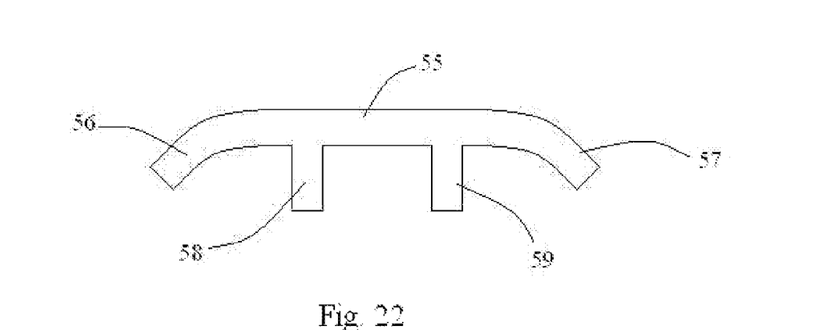
FIG. 22 is a side view of another embodiment of the plate.
Figure 23:
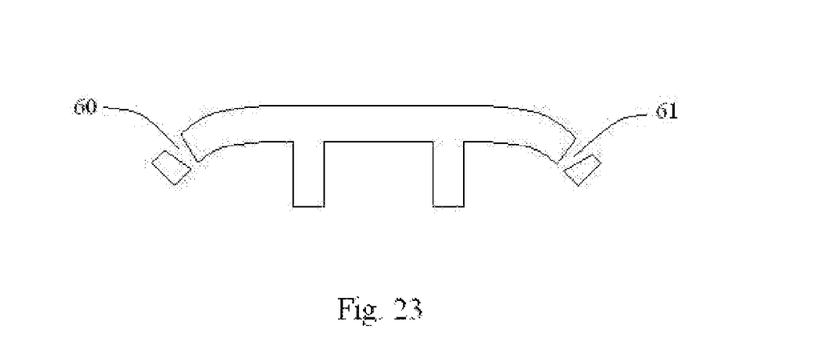
FIG. 23 is a sectional side view of the plate.
Figure 24:
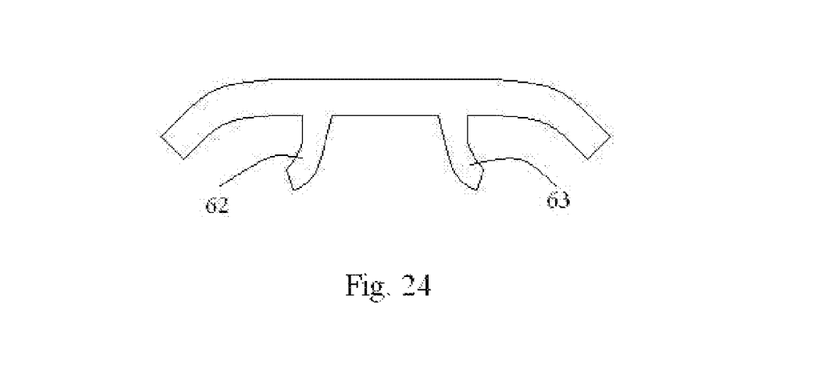
FIG. 24 is a side view of another embodiment of the plate.

The trap door laminoplasty implant can comprise of straight or curved appendages. FIGS. 22 and 23 illustrates the implant with a central portion 55 and angled ends 56 and 57 with screw holes 60 and 61 for fixation to the lamina. The appendages 58 and 59 in the middle are straight. FIG. 24 illustrates the implant with curved appendages 62 and 63. Other embodiments of the implant can also comprise of hook shaped appendages to secure the lamina ends.

Figure 25:
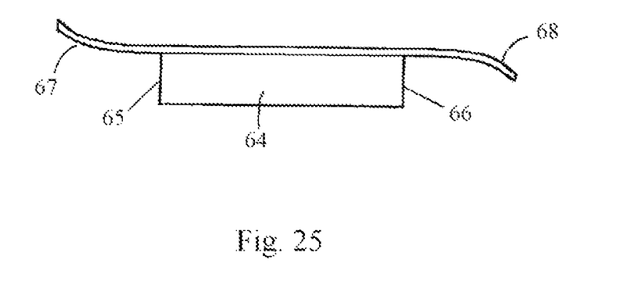
FIG. 25 is a side view of another embodiment of the plate with a spacer.
Figure 26:
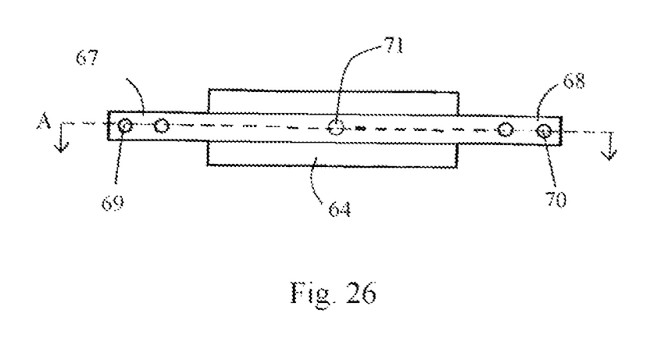
FIG. 26 is a top view of the device shown in FIG. 25.
Figure 27:
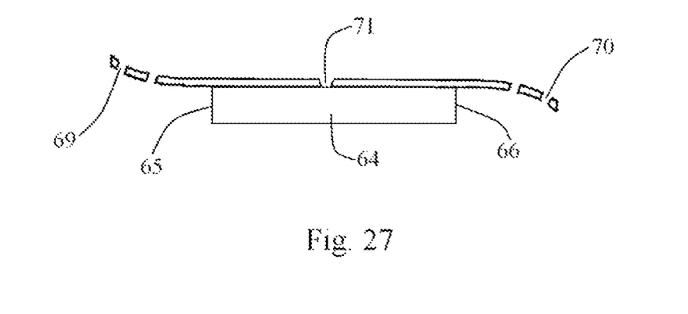
FIG. 27 is a sectional side view of the device taken along line A in FIG. 26.

In one embodiment of the trap door laminoplasty fusion device as illustrated in FIGS. 25-27, the device has a spacer in the middle 64, an end 65 that engages with the facet, and an end 66 that engages with the displaced lamina edge. The plates at the distal ends are angled upwards 67 at one end with screw holes 69 to allow fixation to the facet via a screw and angled downwards 68 with screw holes 70 to allow fixation to the lamina via a screw. The spacer 64 in the middle is attached to the plate with a screw through the screw hole 71. The spacer is made of a fusion material like allograft bone, autograft bone, xenograft bone, bone morphogenic protein, or hydroxyapatite to fuse the lamina in the fixed position provided by the device.

Figure 28:
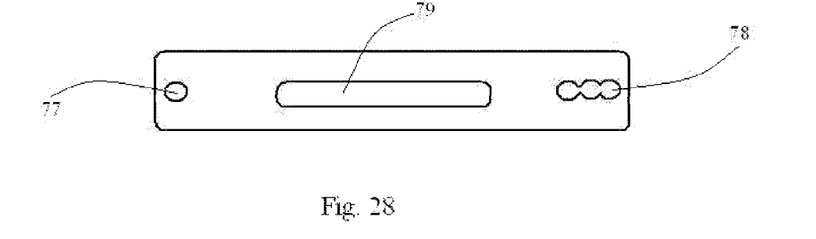
FIG. 28 is a top view of another embodiment of the unitary plate and spacer device.
Figure 29:
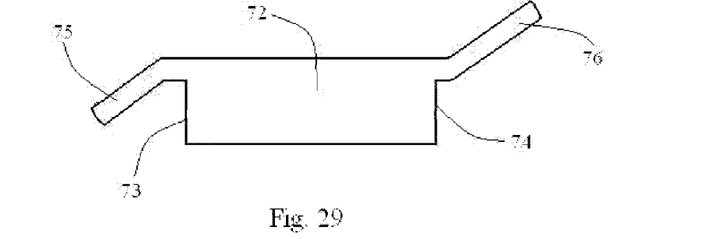
FIG. 29 is a side view of the device.
Figure 30:
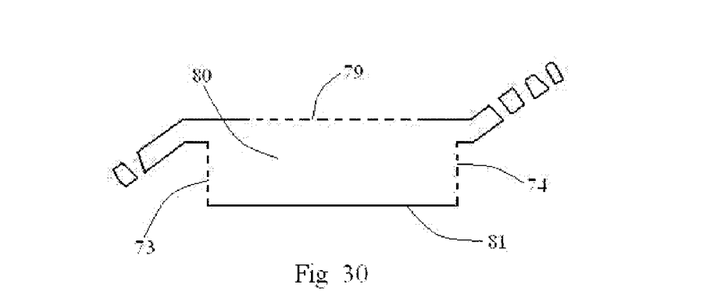
FIG. 30 is a sectional side view of the device.

In another embodiment of the trap door laminoplasty fusion device as illustrated in FIGS. 28-30, the device has a spacer in the middle with a top surface opening 79, one end 74 that engages with the facet, and another end 73 that engages with the lamina. The plate is angled upwards 76 at one end with screw holes 78 to allow fixation to the facet via a screw and angled downwards 75 at the other end with screw hole 77 to allow fixation to the lamina via a screw. The spacer in the middle is hollow 80 with a top contiguous with the plate. The hollow spacer has open ends 73 and 74. The spacer can be packed with a fusion material like allograft or autograft bone, bone morphogenic protein, or hydroxyapatite to fuse the lamina to the facet in the fixed position provided by the device. The spacer has a partial or complete opening 79 at the top to allow for packing of the bone fusion material and a solid floor 81 to prevent migration of the fusion material into the spinal canal.

Figure 31:
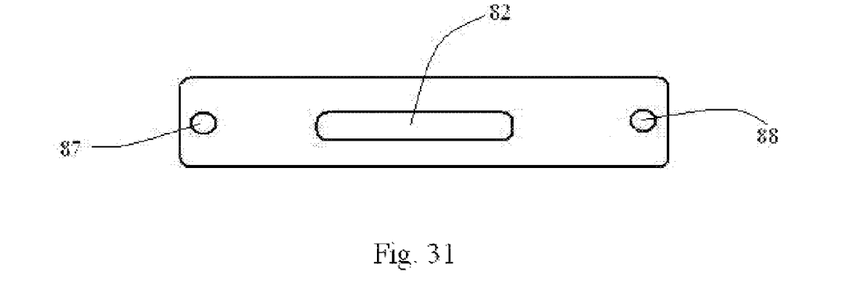
FIG. 31 is a top view of another embodiment of the unitary plate and spacer device.
Figure 32:
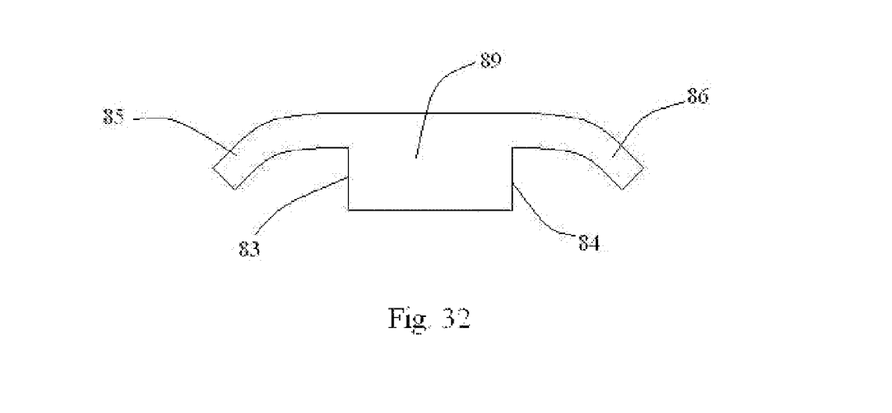
FIG. 32 is a side view of the device.
Figure 33:
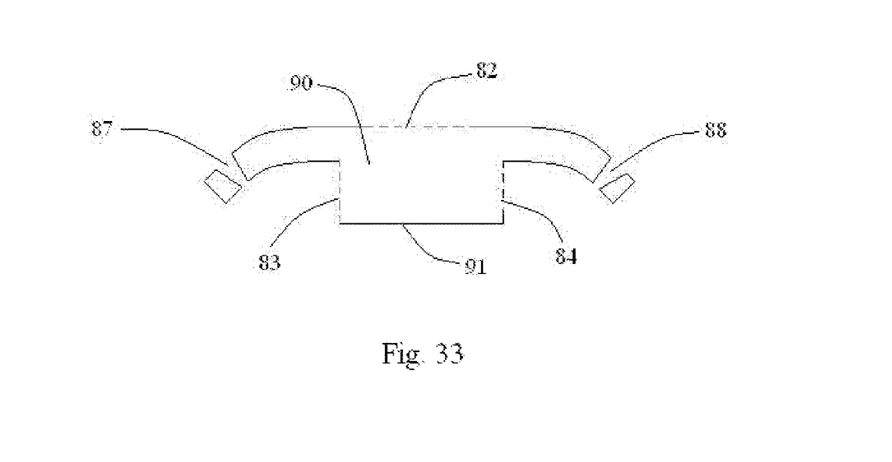
FIG. 33 is a sectional side view of the device.

In one embodiment of the open door laminoplasty fusion device as illustrated in FIGS. 31-33, the device has a spacer 89 in the middle with a top surface opening 82, one end 83 and another end 84 that engage with the lamina. The plate is angled downwards 85 and 86 at both ends with screw holes 87 and 88 to allow fixation to the lamina via a screw. The spacer 89 in the middle is hollow 90 with a top contiguous with the plate. The hollow spacer has open ends 83 and 84. The spacer can be packed with a fusion material like allograft or autograft bone, bone morphogenic protein, or hydroxyapatite to fuse the lamina in the fixed position provided by the device. The spacer has a partial or complete opening 82 at the top to allow for packing of the bone fusion material and a solid floor 91 to prevent migration of the fusion material into the spinal canal.

Figure 34:
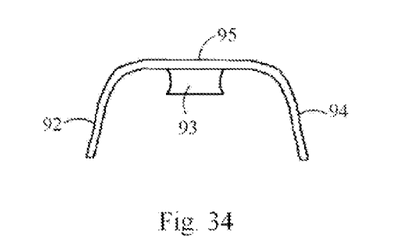
FIG. 34 is a side view of another embodiment of the plate with a spacer.

In another embodiment of the open door laminoplasty fusion device as illustrated in FIG. 34, the device has downward angled distal ends 92 and 94 and a bone fusion spacer 93 in the middle attached to the central plate portion 31 with a biocompatible adhesive.

Figure 35:
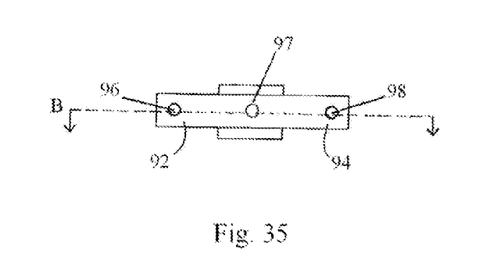
FIG. 35 is a top view of another embodiment of the plate with a spacer.
Figure 36:
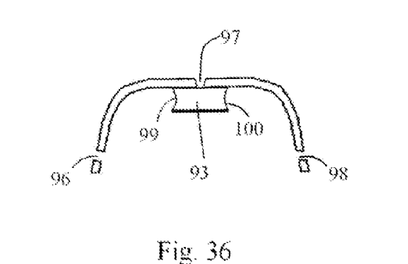
FIG. 36 is sectional side view taken along line B in FIG. 35.
Figure 37:
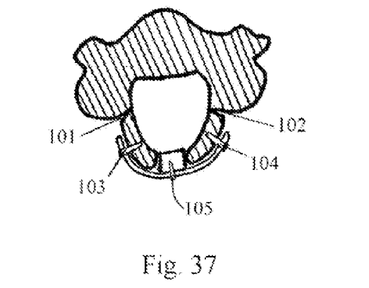
FIG. 37 is a cross section of the vertebra following a trap door laminoplasty with the device shown in FIG. 35 in place.

In another embodiment as shown in FIGS. 35-37, the plate at the distal ends is angled with screw holes 96 and 98 to allow fixation to the lamina via screws. The spacer 93 in the middle is attached to the plate with a screw through the central plate screw hole 97. The spacer ends 99 and 100 engage the lamina ends. The spacer is made of a fusion material like allograft bone, autograft bone, or bone morphogenic protein. The open door laminoplasty technique as shown in FIG. 37 involves removal of the spinous process and creation of unicortical laminoplasty grooves 101 and 102 at the junction of the lamina and facet on both sides. The displaced lamina are then maintained in that position with the device with a spacer in the middle secured to the plate with the bone screw 105. The fusion device also has plates with bone screw receiving holes that allow fixation of the plate with bone screws 103 and 104 securing the device to the lamina.

Figure 38:
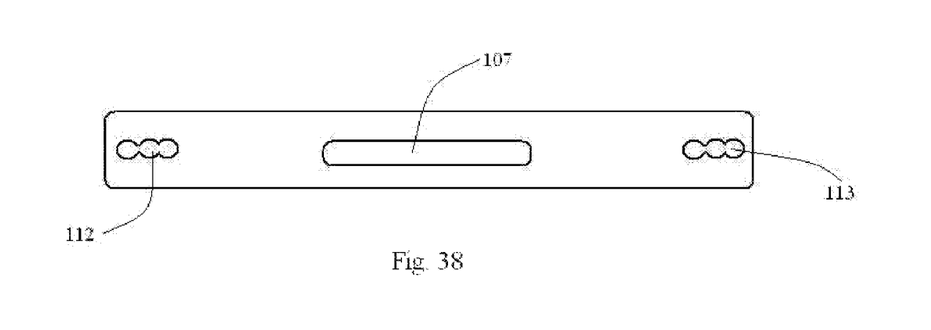
FIG. 38 is a top view of another embodiment of the unitary plate and spacer device.
Figure 39:
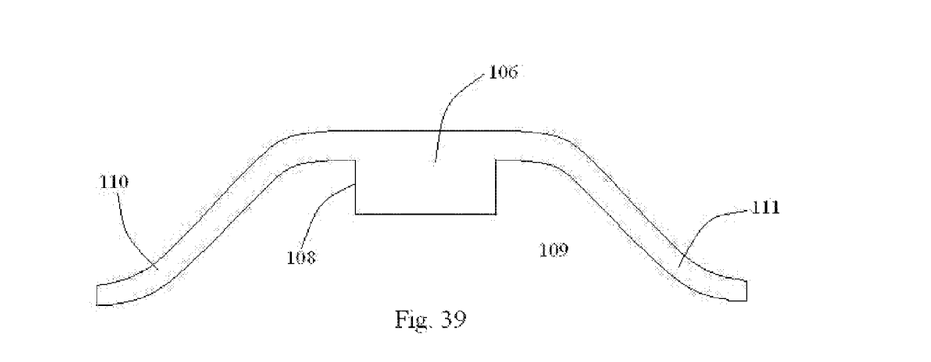
FIG. 39 is a side view of the device.
Figure 40:
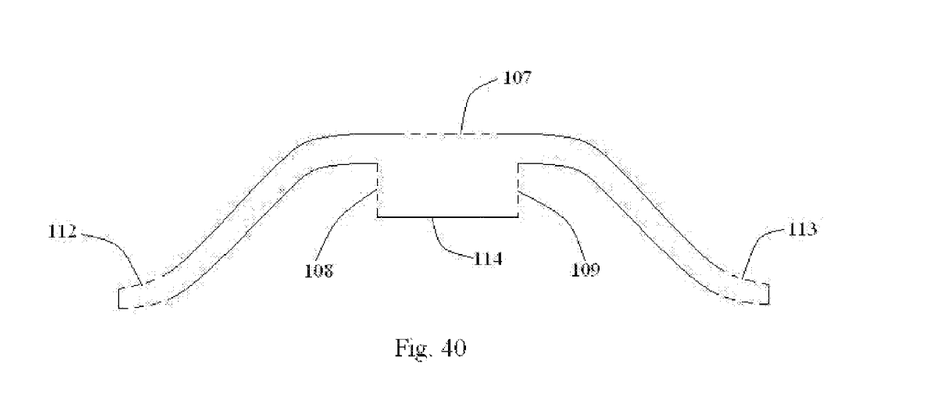
FIG. 40 is a sectional side view of the device.

In another embodiment of the open door laminoplasty fusion device as illustrated in FIGS. 38-40, the device has a spacer 106 in the middle with a top surface opening 107, one end 108 and another end 109 that engage with the lamina. The plate has a lazy L-shape 110 and 111 on both sides with screw holes 112 and 113 to allow fixation to the facets via a screw. The spacer 106 in the middle is hollow with a top contiguous with the plate. The hollow spacer has open ends 108 and 109. The spacer can be packed with a fusion material like allograft or autograft bone, bone morphogenic protein, or hydroxyapatite to fuse the lamina in the fixed position provided by the device. The spacer has a partial or complete opening 107 at the top to allow for packing of the bone fusion material and a solid floor 114 to prevent migration of the fusion material into the spinal canal.

Figure 41:
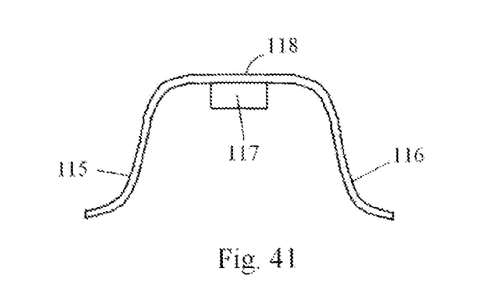
FIG. 41 is a side view of another embodiment of the plate with a spacer.
Figure 42:
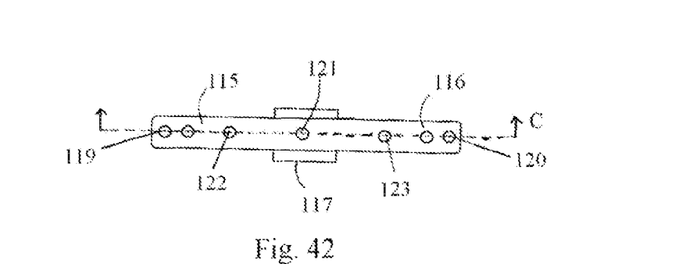
FIG. 42 is a top view of another embodiment of the plate with a spacer.
Figure 43:
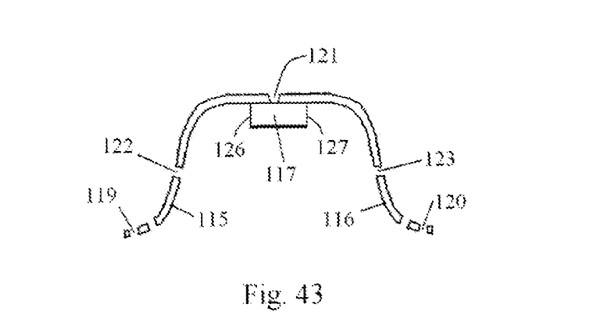
FIG. 43 is sectional side view taken along line C in FIG. 35.
Figure 44:
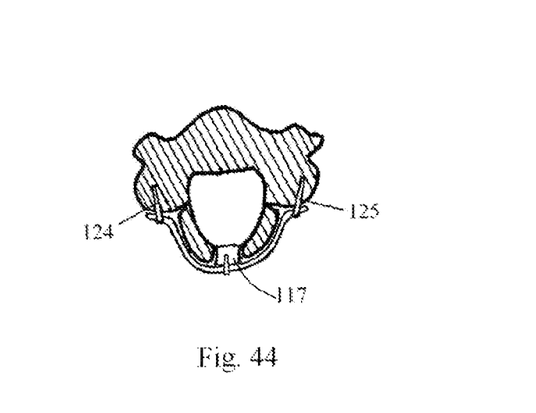
FIG. 44 is a cross section of the vertebra following a trap door laminoplasty with the device shown in FIG. 42 in place.

In another embodiment of the laminoplasty fusion device for the open door laminoplasty technique as illustrated in FIGS. 41-44, the device has a spacer in the middle 117 and ends 115 and 116 that engage with the facet with screws. The plates at the distal ends are angled both ends with screw holes 119 and 120. The spacer 64 in the middle is attached to the plate 118 either with a biocompatible adhesive as shown in FIG. 41 or a screw placed through the central plate hole 121. The spacer is made of a fusion material like allograft bone, autograft bone, xenograft bone, bone morphogenic protein, or hydroxyapatite to fuse the lamina in the fixed position provided by the device. The plate also has screw holes 122 and 123 if needed for screw placement into the lamina. FIG. 44 illustrates the lamina fusion device in place following an open door laminoplasty. The displaced lamina are then maintained in that position with a lamina fixation device with a spacer in the middle 117 with the plate fixated to the facets through bone screws 124 and 125.

The length of the plates as well as the spacer can vary depending on the laminar displacement desired by the surgeon with either the open door or trap door laminoplasty technique.

The laminoplasty plates can be made of metal, polymers, ceramics, composites, and/or any bio-compatible material with sufficient strength to maintain the open position of the divided lamina. The plates can be constructed of titanium or titanium alloy for MRI imaging compatibility. It could also be made of a bio-absorbable material (polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, and para-dioxanone), or allograft or xenograft bone that is absorbed by the body over time once the divided lamina have fused. Alternatively, it could be made of a radiolucent material (polyetheretherketone), plastic, or a combination of plastic and metal to reduce CT and MRI imaging artifact.

The laminoplasty plates can be of a unitary construction, such that the spacer portion, lamina engaging portions and/or the facet engaging portions can be integral or formed from a single piece of material. Alternative embodiments contemplate that the components of the laminoplasty plate can be non-integral, and can be attached to and/or coupled to other components of laminoplasty plate.

The spacer can be made of any bio-compatible material, including autograft, allograft or xenograft, and can be resorbable or non-resorbable in nature. Bone fusion material can include demineralized bone matrix, bone morphogenic protein, hydroxyapatite, and combinations thereof. Resorbable materials can include polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK (polyetheretherketone), and PEAK (polyaryletherketone) composites, shape-memory alloys like nitinol, titanium, titanium alloys, cobalt chrome alloys, stainless steel, ceramics and combinations thereof and others as well.

While the present invention has been described in conjunction with preferred embodiments and methods, it is intended that the description and accompanying drawings shall be interpreted as only illustrative of the invention. It is evident that those skilled in the art may make numerous uses and modifications of and departures from the specific embodiments described herein without departing from the inventive concept.

The invention claimed is:

1. A method for securing lamina after laminoplasty, the method comprising the steps of performing a laminoplasty procedure producing a space between the lamina and the facet; providing an elongated plate adapted for engaging portions of the lamina and the facet, wherein the plate includes a hollow spacer, the hollow spacer including fusion material; engaging portions of the lamina and the facet; and fastening the plate to the lamina and the facet.

2. The method of claim 1, wherein the plate comprises magnetic resonance compatible material.

3. The method of claim 1, wherein the fusion materials is selected from the group consisting of allograft bone, autograft bone, xenograft bone, bone morphogenic protein, and hydroxyapatite.

4. The method of claim 1, wherein the spacer includes at least one opening at the top to receive materials and a solid floor to prevent migration of the material into the spinal canal.

5. The method of claim 1, wherein the plate is individually configured for each patient's anatomy.

6. The method of claim 1, wherein the elongated plate having at least one appendage portion for engaging a portion of the lamina.

7. The method of claim 1, wherein the elongated plate having at least one appendage for engaging a portion of the facet.

8. The method of claim 1, wherein the elongated plate terminates with an upwardly extending portion for engaging a portion of the facet.

9. The method of claim 8, further including the step of fastening the upwardly extending portion to portions of the lamina.

10. The method of claim 1, wherein the elongated plate terminates with a downwardly extending portion for engaging a portion of the lamina.

11. The method of claim 1, wherein the elongated plate including at least one appendage to secure the elongated plate to a portion of the lamina.

12. The method of claim 11, further including the step of securing the at least one appendage to a portion of the lamina.

13. A method for securing lamina after laminoplasty, the method comprising the steps of performing a laminoplasty procedure producing a space between the lamina and the facet; providing an elongated plate adapted for engaging portions of the lamina and the facet, wherein the elongated plate having at least one appendage portion for engaging a portion of the facet, and wherein the elongated plate terminates with an upwardly extending portion for engaging a portion of the lamina; and fastening the plate to a portion of the lamina and the facet.

14. The method of claim 13, wherein the elongated plate includes a hollow spacer, and wherein the hollow spacer including fusion material.

15. The method of claim 13, wherein the fusion materials is selected from the group consisting of allograft bone, autograft bone, xenograft bone, bone morphogenic protein, and hydroxyapatite.

16. The method of claim 13, wherein the plate is individually configured for each patient's anatomy.

17. The method of claim 13, wherein the elongated plate having at least one appendage portion for engaging a portion of the lamina.

18. The method of claim 13, wherein the elongated plate having at least one appendage for engaging a portion of the facet.

* * * * *